United States Patent [19]

Capanna et al.

[11] Patent Number: 4,955,508
[45] Date of Patent: Sep. 11, 1990

[54] CONTAINER AND METHOD FOR WASHING AND EFFECTIVELY COMPLEMENTING THE OPERATION OF DIALYSIS CIRCUITS AND FILTERS

[75] Inventors: Dario Capanna, Milan; Alfredo Romeo, Segrate; Luigi Mescia, Sondrio, all of Italy

[73] Assignee: Pierrel Hospital Spa, Sondalo, Italy

[21] Appl. No.: 743,823

[22] Filed: Jun. 12, 1985

[30] Foreign Application Priority Data

Jun. 25, 1984 [IT] Italy .............................. 21580 A/84

[51] Int. Cl.⁵ .............................................. B65D 35/22
[52] U.S. Cl. ..................................... 222/94; 222/478; 222/564; 383/38
[58] Field of Search ................. 222/94, 107, 481, 478, 222/564; 383/38–41, 100–101, 906

[56] References Cited

U.S. PATENT DOCUMENTS

| | | |
|---|---|---|
| 3,105,613 | 10/1963 | Barton et al. .................... 222/481 X |
| 3,304,977 | 2/1967 | Hammons ......................... 383/38 X |
| 3,537,455 | 11/1970 | Skyles et al. ......................... 128/275 |
| 3,542,032 | 11/1970 | Spencer, Jr. ..................... 383/38 X |

FOREIGN PATENT DOCUMENTS 21424  5/1883  Fed. Rep. of Germany ........ 383/38

Primary Examiner—Michael S. Huppert
Attorney, Agent, or Firm—Armstrong, Nikaido, Marmelstein, Kubovcik & Murray

[57] ABSTRACT

A container in the form of a soft plastic bag divided into at least two and possibly three non-communicating chambers. The first two chambers may contain predetermined quantities of physiological salt washing solution for the extracorporeal circuit on the blood side of a dialysis apparatus before employment of the apparatus in dialysis. Physiological salt solution in the first chamber may be used for washing the circuit by recirculation, if necessary, after an initial quantity of physiological salt solution has passed through the circuit and has been removed or discharged into the third chamber. Physiological salt solution in the second chamber may be utilized to complete the washing of the circuit and, if necessary, for replacement of water in the patient's blood to the patient's body at the end of the dialysis.

5 Claims, 6 Drawing Sheets

CONTAINER AND METHOD FOR WASHING AND EFFECTIVELY COMPLEMENTING THE OPERATION OF DIALYSIS CIRCUITS AND FILTERS

The present invention relates to a container or bag designed to deliver a detergent or washing solution to dialysis equipment circuits and filters as well as a method of washing said circuits and filters.

It is known that in extracorporeal dialysis the use of plastic circuits and filters to be used for a single treatment cycle and discarded after use has become continually better established over the years. More specifically this trend has developed for those components of the dialysis equipment which come in contact with the patient's blood.

Said circuits and filters are made of appropriate plastic materials and before use, i.e. before connection to the internal circulatory system of the patient, must be washed with a physiological salt soltion, for example a 0.9% solution of NaCl, to eliminate residual traces of substances used during manufacture and completion, in particular sterilization, of the circuits and filters in question, such as for example glycerol, ethylene oxide, etc.. This is not only advisable therapeutically since even traces of the substance considered can be toxic or at least not suitable for patients who are subjected to blood purification, but also imposed by specific health standards.

As these circuits and filtes are supplied in sterile conditions and packages the procedure followed until now consists of washing, which requires 20–30 minutes, shortly before the dialysis session, connecting the inlet or arterial end of thge blood circuit, including the series-mounted filter, to one or more bottles of sterile physiological salt solution and causing the solution to flow through the circuit with discharge at the other, venous, end, following a procedure which despite the fullest attention of the operator can no longer assure perfect sterility of the circuit after washing, particularly if for any reason the beginning of the dialysis session is delayed.

The problem is obviously still more complicated if a certain number of patients are to undergo dialytic treatment simultaneously.

Another presently known and followed procedure consists of recirculation of the physiological salt solution which however can result in traces of the substances to be eliminated being returned to circulation with the obvious drawbacks.

On the other hand if the circuit including the filter is not used immediately it shoud be prevented from drying out because damage to the membranes or unforeseen resistances to extracorporeal blood circulation could arise.

Another problem is to avoid a part of the physiological salt solution used for washing being mixed with the blood entering the extracorporeal circuit at the beginning of the dialysis cycle.

Another problem connected with the actual dialysis lies in the fact that due for example to ultrafiltration phenomena the patient is impoverished in water and nontoxic salts so that it is sometimes necessary to replace this liquid during dialysis.

All these problems and drawbacks are solved by the method and container according to the present invention.

The container in particular is characterized in that it comprises at least two chambers or recesses independent of each other and noncommunicating, one of said chambers having an inlet fitting and a discharge fitting from and to the exterior respectively connectable to the extracorporeal blood circuit of the dialysis apparatus and the other i.e. the second of said chambers being equipped with a single fitting for connection to the exterior.

In the preferred embodiment of the container according to the invention in said first chamber are provided means preferably located between the internal openings of said two fittings for bringing about a flow from one opening to the other which involves the entire chamber, thus preventing a short circuit in the flow between the two openings and stagnation of the liquid present in the rest of the chamber.

Furthermore in conformance with another variant of the invention with said two chambers is associated a third chamber normally empty and equipped with a fitting for connection to the dialysis equipment circuit.

The invention also provides a method of washing the extracorporeal circuit on the blood side of the dialysis apparatus which is characterized in that the ends of the circuit are connected to said two fittings of said first chamber and the physiological salt washing solution contained therein is made to circulate continuously through said circuit by means of a blood circulation pump with which the circuit is equipped, the circulation being maintained until the circuit is connected after a last emptying to the inlet and outlet fittings of the blood to be subjected to dialysis.

In conformance with another embodiment of the method of the invention part of the physiological salt washing solution corresponding to a predetermined portion of the content of said first chamber and which is the first to pass through said circuit is discharged and discarded or else is discharged into said empty chamber after having passed through and washed the entire dialysis circuit on the blood side, after which it resumes continuous recirculation as indicated above.

According to another variant of the method according to the invention before connection of the dialysis circuit to the blood inlet and outlet fittings a last washing with fresh physiological salt solution taken from said second chamber is performed.

According to another aspect of the method of the invention the fresh physiological salt solution of said second chamber is used to inject into the circuit during predetermined quantities of the same solution containing if desired additional substances and/or drugs.

The peculiar aspects and benefits of the present invention will appear more clearly from the following detailed description made in relation to the preferred embodiments and with reference to the annexed drawings, wherein.

Figure 1:
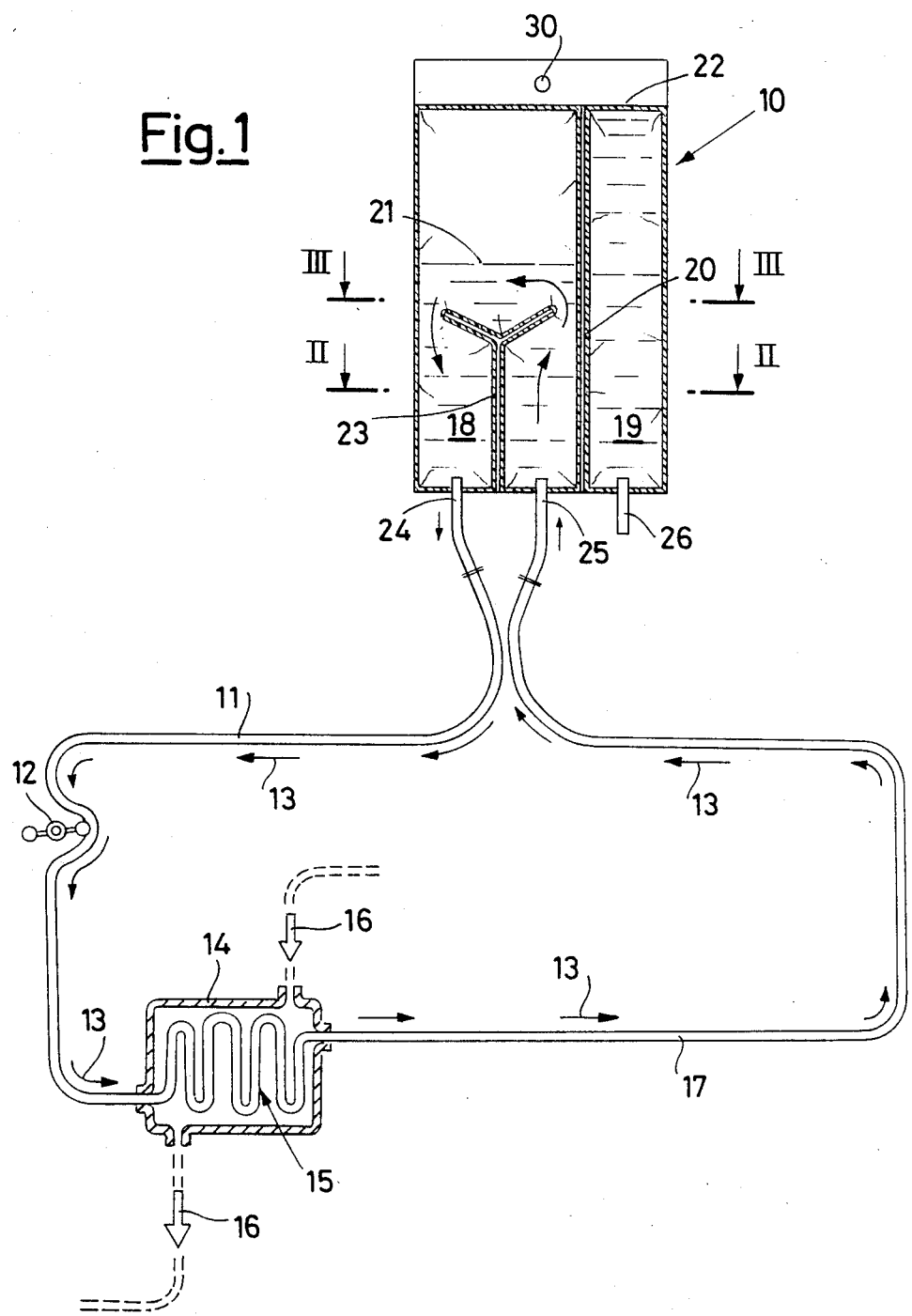
FIG. 1 is a schematic view of the container of the invention in operating condition.
Figure 2:
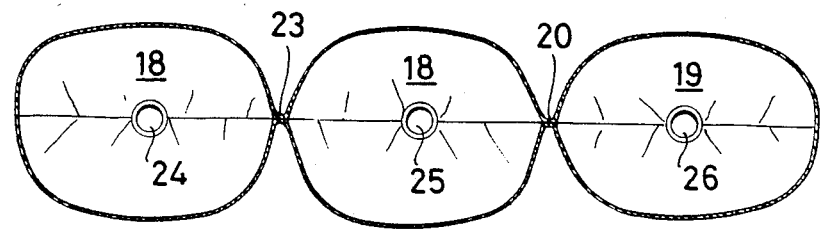
FIGS. 2 and 3 are cross sections along planes II—II and III—III respectively of FIG. 1.
Figure 3:
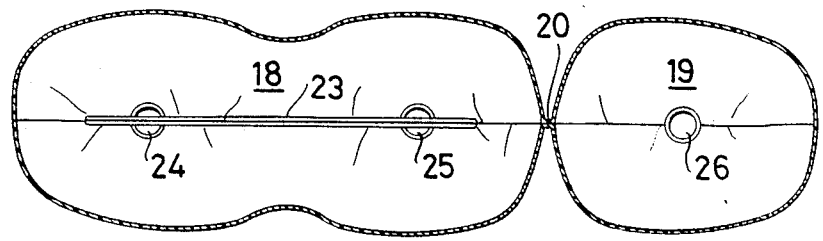

Referring first to FIG. 1 a container 10 is shown with a generic connection to the extracorporeal circuit on the blood side of the dialysis apparatus which for drawing simplicity and clarity is not shown in detail.

The dialysis apparatus comprises a circuit branch 11 in which is inserted a pump 12 for example of the roll type which provides circulation in the direction shown by the arrow 13.

The circuit then comprises a dialysis unit 14 containing a filter 15 of the semipermeable membrane type, the unti 14 being equipped with inlet and outlet fittings for the dialytic solution as shown by the arrow 16.

At the outlet of the unit 14 is provided a second branch 17 of the circuit.

Since the circuit briefly described above is a well known conventional type particularly as regards the type of plastic used, to be used only once and discarded, it will not be described in greater detail. The same consideration applies to the semipermeable membrane used in the dialysis unit 14.

The container 10 is preferably accomplished in the form of a soft plastic bag in which are set off chambers and specifically a first chamber 18 and a second chamber 19.

The partition 20 between the two chambers is preferably accomplished in the form of a water-tight weld between the two opposing walls, in particular in the form of two parallel welds.

A similar weld 22 completes the chambers 18 and 19 while reference number 21 indicates a liquid level in the chamber 18 which is then partially filled in order to be able to receive an additional portion of liquid.

In the chamber 18 is also formed a partial separation baffle 23 preferably in the shape of a Y positioned between the two fittings 24 and 25 which connect the chamber 18 with the exterior for the purpose explained below.

The fittings 24 and 25 are provided with closures with prefracture cones designed to assure sterility and optimal flow, and valves e.g. of the clamp type which can be opened and closed at will e.g. of the type used for phleboclyses and therefore not illustrated it being intended that the connection to an outside tube of the individual fittings means also that their open condition is regulated by the greater or lesser compression applied by the associted clamp valve.

The baffle 23 is also preferably accomplished by heat welding of the two opposed walls and this makes clear the simplicity and low production cost of the container 10.

The chamber 19 is in turn equipped with a fitting 26.

Figure 4:
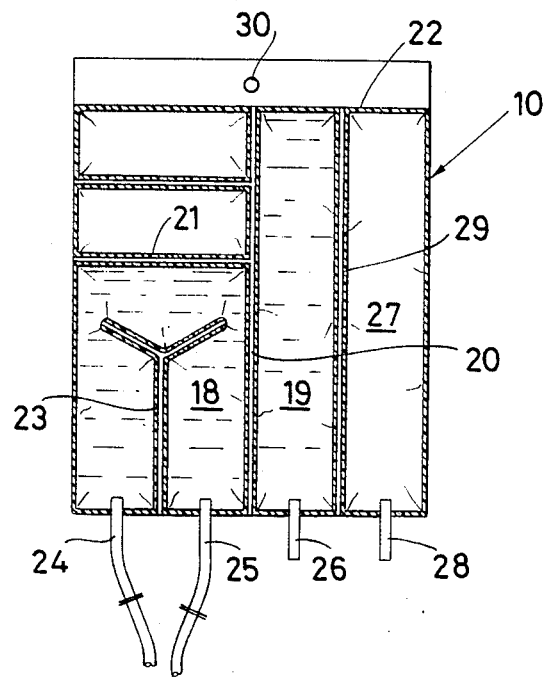
FIG. 4 is a partially sectional front view of another embodiment of the container of the invention.

Now referring to FIG. 4 a variant of the container 10 is shown providing an added chamber 27 with a fitting 28 and separated from the adjacent chamber 19 by a baffle 29 accomplished likewise by heat welding.

In the container 10 an upper eye 30 makes it possible to fix the container on a suitable support which is not shown.

Figure 5:
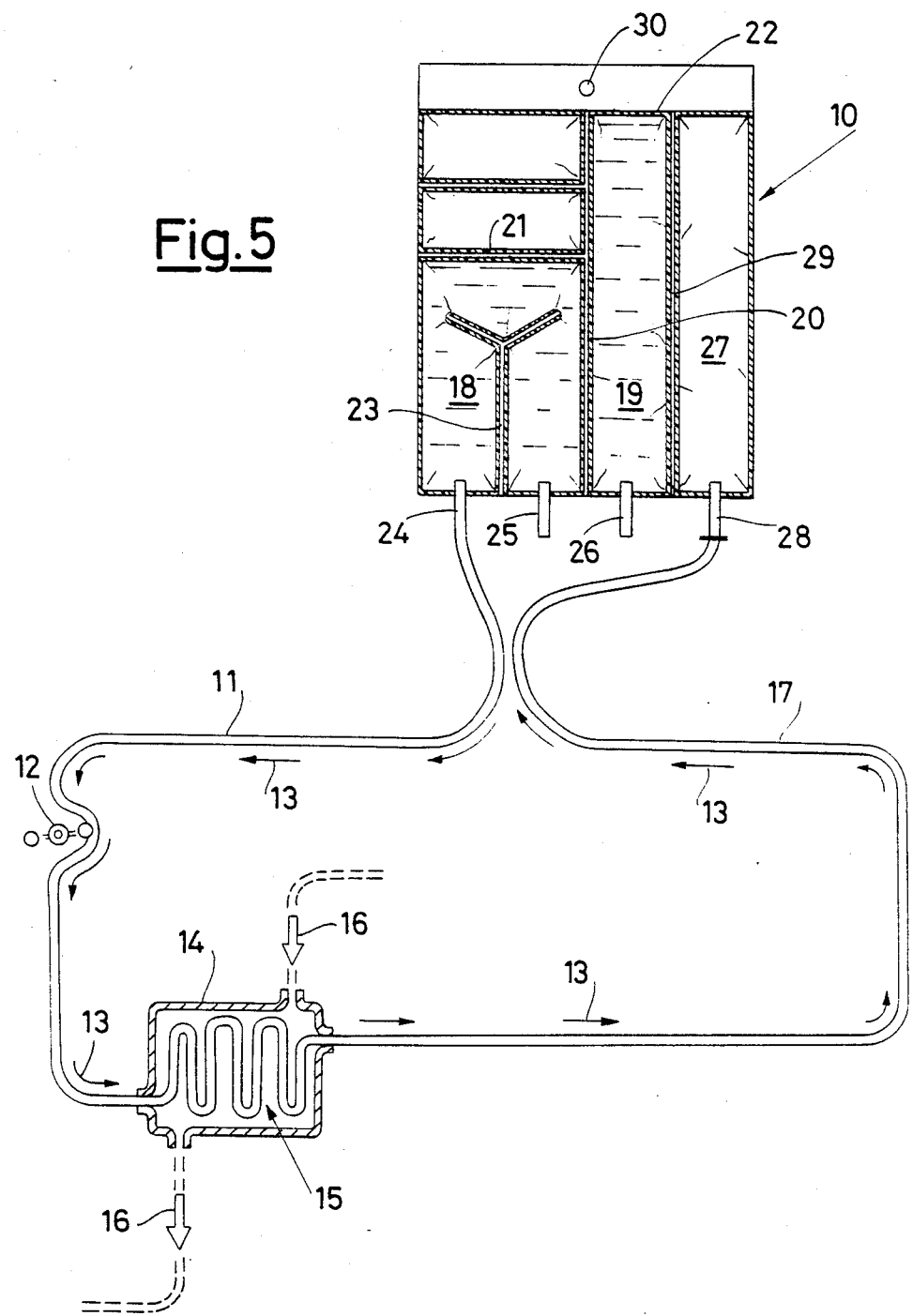
FIGS. 5, 6, 7 and 8 illustrate the divers conditions and operational relationship of the method of the invention.
Figure 6:
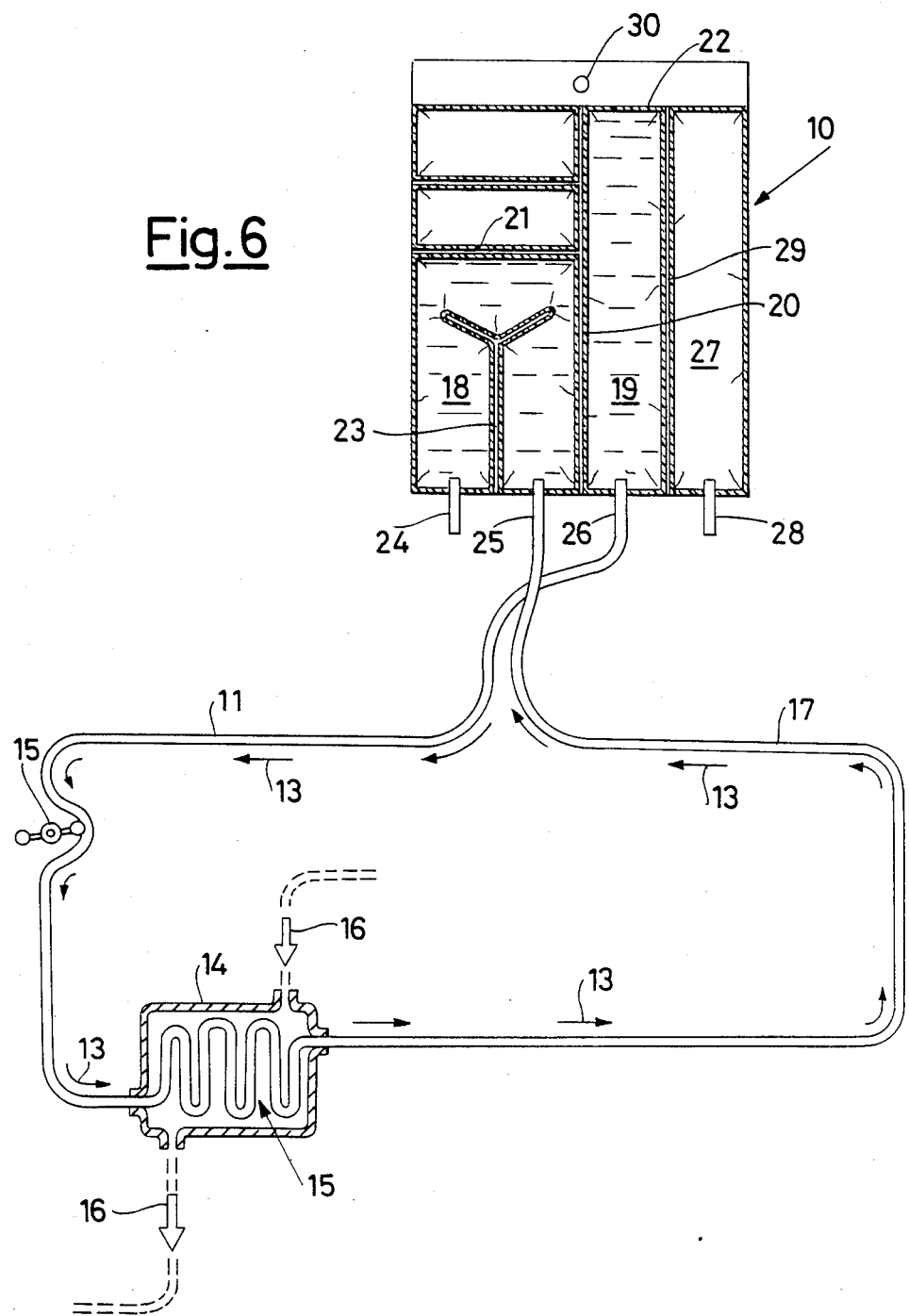
Figure 7:
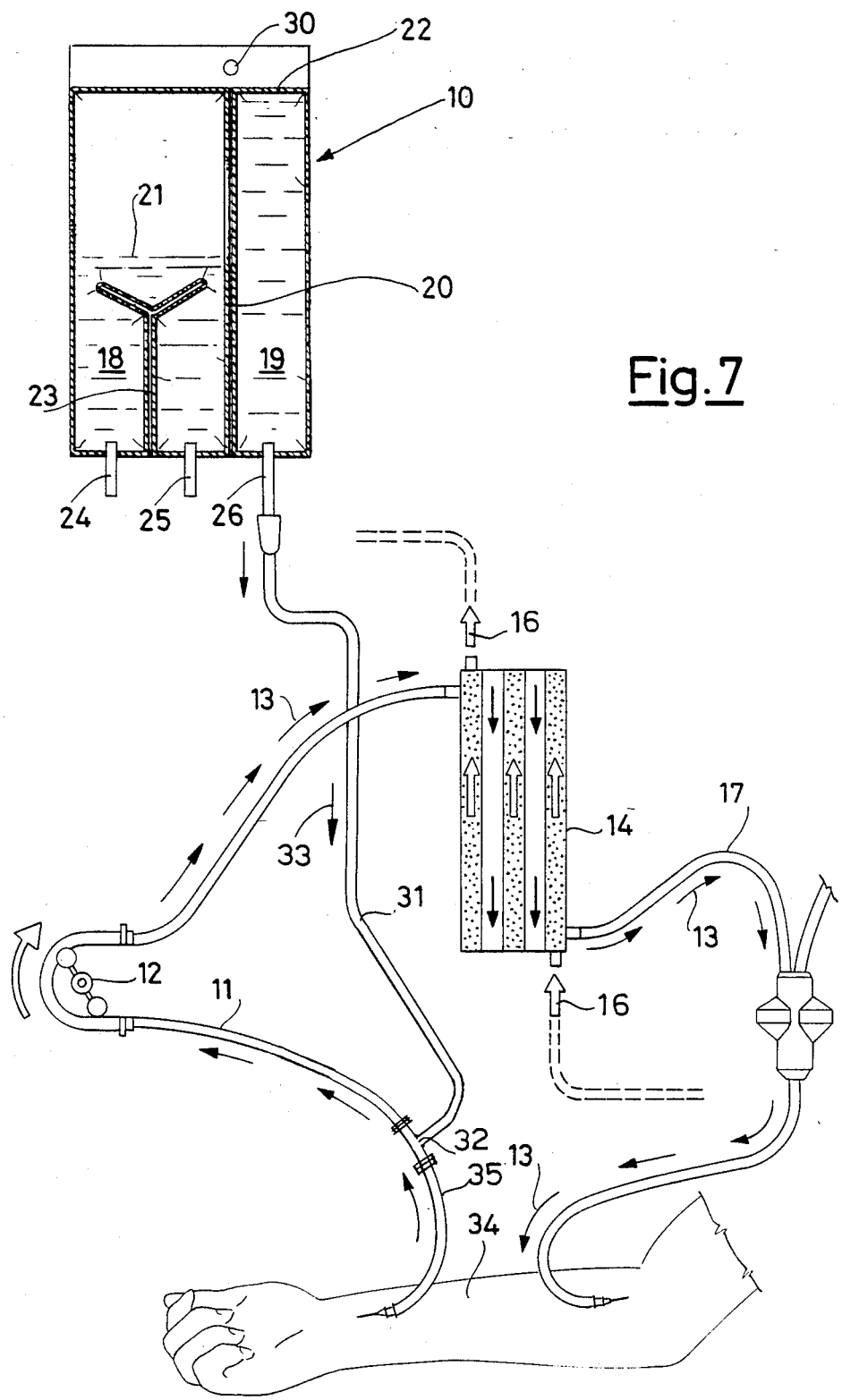

Now referring to FIGS. 5—8 the steps of the method of the invention are illustrated diagrammatically with the use of the container of FIG. 4 it being understood that similar conditions and considerations are applicable using the container of FIG. 1 as in FIG. 7.

In the first step the circuit is connected with its branch 11 to the fitting 24 of the chamber 18 and with its branch 17 to the fitting 28 of the empty chamber 27.

Starting the roller pump 12 the solution contained in the chamber 18 beings to pass through the circuit and the dialysis unit 14, circulation on the dialytic solution side being closed, washing them and entering the chamber 27.

When a predetermined quantity of washing solution on the order to example of 200–300 cc has reached the chamber 27 and hence a large part of the toxic substances has been washed away the branch 17 is connected to the fitting 25 as shown in FIG. 1 and the residual solution contained in the chamber 18, a volume of approximately 1000 cc, is circulated continuously through the entire circuit from the blood side until the circuit is to be connected to the patient.

The baffle 23 ensures that all the solution in the chamber 18 participates in the washing without stagnation.

It is clear that operationally the circuit is set from the start in the operative condition of the dialytic apparatus except that connection to the container 10 and passage from the washing step to use does not involve a shift or stop of any kind and this promotes sterility and operating efficiency.

Shortly before the circuit is to be put to use the branch 11 is connected to the fitting 26 of the chamber 19 in FIG. 6 so that fresh new solution pushes the solution which circulated in the circuit into the chamber 18 through the fitting 25, completing washing of the circuit.

When using the container shown in FIG. 1 because for example the content of residual toxic substances in the circuit to be washed is sufficiently low the step illustrated in FIG. 5 is omitted and all the solution contained in the chamber 18 recycles through the circuit until the final washing with fresh solution coming from the chamber 19.

Figure 8:
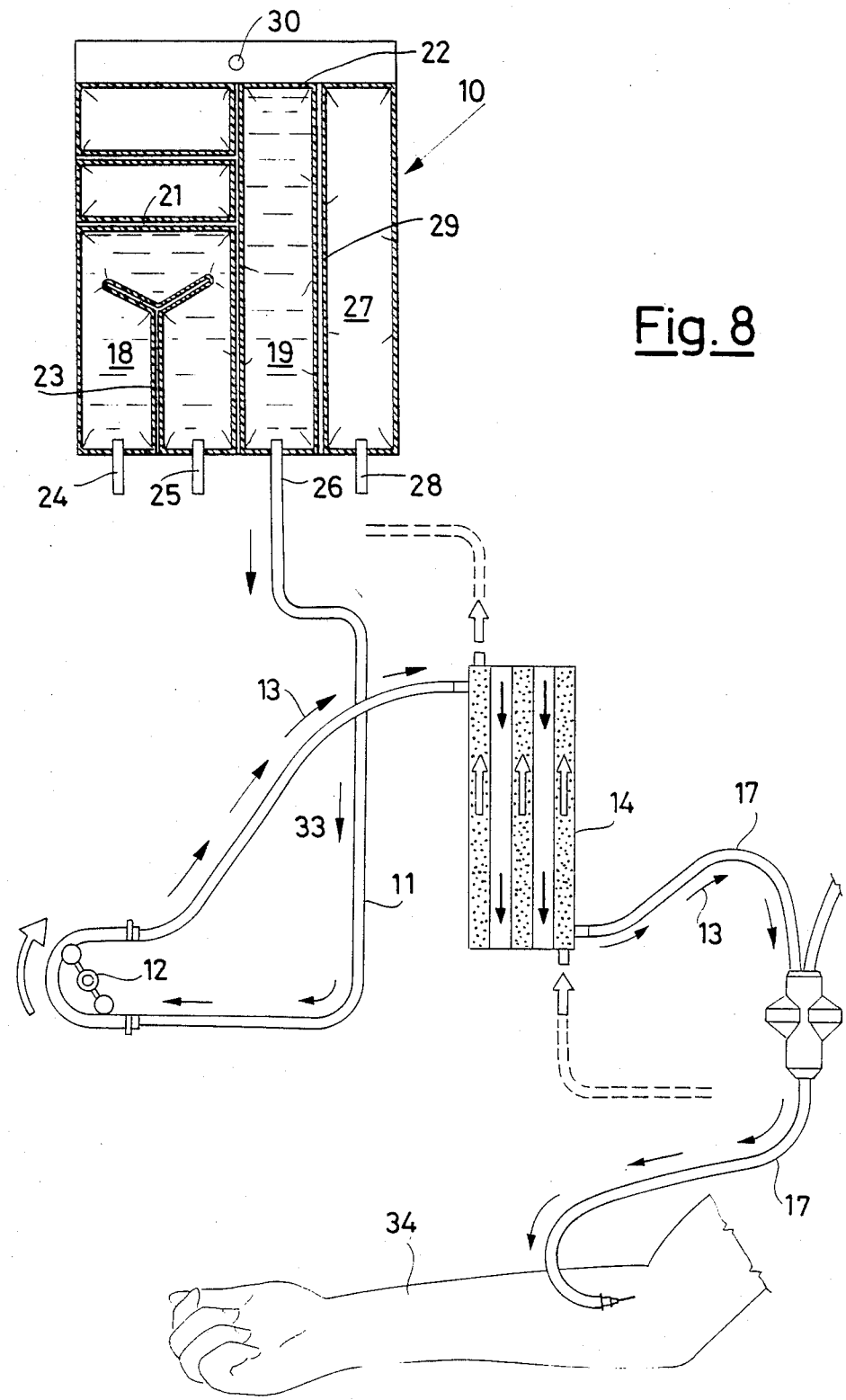

FIGS. 7 and 8 illustrate two other operating conditions peculiar to the method of the invention.

Referring to FIG. 7 and remembering that as already mentioned there is sometimes a need to top up or complete with water or preferably with physiological salt solution when for example the loss undergone by the patient due to ultrafiltration in the course of dialysis is large, it is possible as shown in FIG. 7 to connect chamber 19 containing fresh physiological salt solution through the fitting 26 and a circuit section 31 to a branch 32 of a known type formed in the branch 11 of the circuit upstream from the pump 12. The pump 12 sucks the physiological salt solution from the chamber 19 and puts it in circulation as indicated by the arrow 33 together with the blood with which it is mixed.

It is clear that if desired to the physiological salt solution contained in the chamber 19 can be added other substances such as for example drugs to sustain the patient's blood pressure and/or combat other pathological or parapathological situations.

Lastly again for the purpose of preventing weakening of the patient or undue loss of blood FIG. 8 shows another operational situation in which at the end of dialysis the connection of the branch 11 of the circuit is switched from the patient's arm 34 to the fitting 26 of the chamber 19 so that continued opertion of the pump 12 sucks into the circuit physiological salt solution which pushes the blood still present in the circuit toward the end of the branch 17 still connected to the vein in the patient's arm. In this manner it is ensured that all the blood is returned to the body circuit of the patient with no danger whatever because if by chance a small quantity of fresh physiological salt solution should enter with the blood it is not dangerous for the patient. Blood can also be returned to the patient's body circuit with the arrangement shown in FIG. 7 without disconnection from the patient's arm.

In this case the length 35 of circuit between the end of the branch 32 and the needle inserted in the patient's artery is clamped for example by means of a loose spring clamp not shown and well known per se. Operation of the pump 12 pushes into the vein through the branch 17 the blood still present in the circuit on the blood side, fresh solution being sucked in through the circuit section 31.

When the whole extracorporeal circuit has been freed from the blood which was returned to the vein the clamp acting on the length 35 is opened and the circuit length between the end of the circuit section 31 and the pump 12 is closed by a similar clamp so that direct communication remains between the chamber 19 and the patient's artery.

The blood contained in the length 35 is then returned by gravity to the artery under the pressure of the solution filling the circuit section 31.

It is important to note that the recovery of even small amounts of blood in quantities of a few milliliters is worth while if allowance is made for the fact that dialytic treatment is repeated several times weekly and blood losses thus accumulate in a short period.

The above description makes clear the structural and functional benefits of the container and of the method of the invention which are reflected not only in the washing of the dialysis circuit on the extracorporeal blood circulation side but also in the performance of the actual dialysis.

From the structural viewpoint the container of the present invention ensures washing under perfectly sterile conditions and maintenance of the circuit in optimal condition for subsequent circulation of dialyzed blood.

Furthermore, accomplishment of the container in the form of a preferably transparent soft plastic bag allows simple and economical industrial production, especially considering the possibility of accomplishing the partitions and the water-tight closure of the container by heat welding.

From the functional viewpoint the method of the invention in combination with the aforesaid container also makes it possible to considerably improve the actual dialyzation, providing a remedy for deficiencies and drawbacks of conventional methods and making it possible to replace if necessary losses of water by the patient and prevent losses of blood however small.

It is understood that conceptually, functionally and structurally equivalent modifications and variants are possible and foreseeable without exceeding the scope of the invention as set forth in the following claims. For example even if the description makes reference to a soft plastic bag container, it is possible and foreseeable to make a rigid container of glass for example which can be reused many times after sterilization.

We claim:

1. A container for washing and operational completion of the extracorporeal blood circuit and filter of dialysis apparatus comprising a first fluid-tight chamber containing a first predetermined quantity of sterile physiological saline solution and a second fluid-tight chamber containing a second predetermined quantity, of sterile physiological saline solution, said first and second chambers being independent of one another and fluidically non-communicating; said first chamber being equipped with two fittings, fluidically connectable to said extracorporeal blood circuit, for inlet to and discharge from said first chamber; said second chamber being equipped with a single fitting, fluidically connectable to said extracorporeal blood circuit, for inlet to and discharge from said second chamber.

2. The container according to claim 1, wherein said container is in the form of a soft thermoplastic bag, said first and second chambers being set off by heat welding between opposing walls of said container.

3. The container according to claim 2, wherein said bag is made of transparent thermoplastic material.

4. The container according to claim 1, wherein a partial baffle is formed within said first chamber, between said two fittings, to guide a flow of liquid between one fitting and the other inside said first chamber.

5. The container according to claim 1, further comprising a third fluid-tight chamber independent of and fluidically non-communicating with said first and second chambers; said third chamber being empty; said third chamber being equipped with a single fitting, fluidically connectable to said extracorporeal blood circuit, for inlet to and discharge from said third chamber.

* * * * *